United States Patent
Xuan et al.

(10) Patent No.: US 12,264,340 B2
(45) Date of Patent: *Apr. 1, 2025

(54) POLYPEPTIDE HAVING PHOSPHOLIPASE C ACTIVITY AND USE THEREOF

(71) Applicant: Wilmar (Shanghai) Biotechnology Research & Development Center Co., Ltd, Shanghai (CN)

(72) Inventors: Yaoji Xuan, Shanghai (CN); Qiwen Niu, Shanghai (CN); Zhengjun Xu, Shanghai (CN)

(73) Assignee: Wilmar (Shanghai) Biotechnology Research & Development Center Co., Ltd, Shanghai (CN)

( * ) Notice: Subject to any disclaimer, the term of this patent is extended or adjusted under 35 U.S.C. 154(b) by 887 days.

This patent is subject to a terminal disclaimer.

(21) Appl. No.: 17/419,082

(22) PCT Filed: Dec. 27, 2019

(86) PCT No.: PCT/CN2019/128973
§ 371 (c)(1),
(2) Date: Jun. 28, 2021

(87) PCT Pub. No.: WO2020/135658
PCT Pub. Date: Jul. 2, 2020

(65) Prior Publication Data
US 2022/0073889 A1    Mar. 10, 2022

(30) Foreign Application Priority Data

Dec. 28, 2018 (CN) .......................... 201811625457.6

(51) Int. Cl.
*C12N 9/16* (2006.01)
*C11B 3/00* (2006.01)
(52) U.S. Cl.
CPC ................ *C12N 9/16* (2013.01); *C11B 3/003* (2013.01); *C12Y 301/04003* (2013.01)
(58) Field of Classification Search
CPC ........... C12N 9/16; C12N 15/81; C11B 3/003; C12Y 301/04003
See application file for complete search history.

(56) References Cited

U.S. PATENT DOCUMENTS

| 2013/0011887 | A1  |   | 1/2013 | Dayton et al. |          |
|--------------|-----|---|--------|---------------|----------|
| 2017/0096619 | A1  | * | 4/2017 | Segura        | C11B 3/00 |

FOREIGN PATENT DOCUMENTS

| CN | 101558154 A     |   | 10/2009 |         |
|----|-----------------|---|---------|---------|
| CN | 102174546 A     |   | 9/2011  |         |
| CN | 105073985 A     |   | 11/2015 |         |
| CN | 106103704 A     |   | 11/2016 |         |
| CN | 106459934 A     |   | 2/2017  |         |
| CN | 106884009 A     |   | 6/2017  |         |
| CN | 108118039 A     |   | 6/2018  |         |
| CN | 109321546       | * | 2/2019  | C11B 3/00 |
| CN | 109321546 A     |   | 2/2019  |         |
| WO | 2011046812 A1   |   | 4/2011  |         |
| WO | 2011046815 A1   |   | 4/2011  |         |
| WO | 2015140275 A1   |   | 9/2015  |         |
| WO | WO 2017/101801  | * | 6/2017  | C12N 9/20 |

OTHER PUBLICATIONS

Translation of CN109321546 retrieved on Apr. 15, 2024 from https://worldwide.espacenet.com/patent/search/family/065245348/publication/CN109321546A?q=pn%3DCN109321546B (Year: 2024).*
U.S. Appl. No. 17/419,091, filed Jun. 28, 2021, Xuan.*
English translation of Xuan WO 2017/101801 retrieved on Nov. 23, 2024 from Esacenet at https://worldwide.espacenet.com/patent/search/family/059055726/publication/WO2017101801A1?q=WO%202017%2F101801 (Year: 2024).*
Database UniProt [Online] Sep. 12, 2018 (Sep. 12, 2018), "RecName: Full=Phospholipase C {ECO:0000256IARBA:ARBA00018391}; EC=3.1.4.3 {ECO:0000256IARBA:ARBA00012018}; AltName: Full=Phosphatidylcholine cholinephosphohydrolase {ECO:00002561 ARBA:ARBA00031285};", XP002807 439, retrieved from EBI accession No. UNIPROT:A0A2B1 YF47 Database accession No. A0A2B1 YF47.
Extended European Search Report for EP 19905362.0, dated Sep. 16, 2022.
Durban et al., High Level Expression of a Recombinant Phospholipase C from Bacillus Cereus in Bacillus Subtilis, Applied Microbiology and Biotechnology, 2007, 74(3):634-639.
Elena et al., B. Cereus Phospholipase C Engineering for Efficient Degumming of Vegetable Oil, Process Biochemistry, 2017, 54:67-72.
Hough et al., High-Resolution (1.5 Å) Crystal Structure of Phospholipase C from Bacillus Cereus, Nature, 1989, 338(6213):357-360.
Johansen et al., Cloning and Sequencing of the Gene Encoding the Phosphatidylcholine-Preferring Phospholipase C of Bacillus Cereus, Gene, 1988, 65(2):293-304.

(Continued)

*Primary Examiner* — Louise W Humphrey
(74) *Attorney, Agent, or Firm* — Quarles & Brady LLP

(57) ABSTRACT

Provided is a polypeptide having phospholipase C activity. The polypeptide has: 1) an amino acid sequence represented by SEQ ID No: 2, comprising amino acid substitutions occurred at one or more positions, wherein the one or more positions are selected from positions 6, 8, 10, 104, and 205 in the amino acid sequence represented by SEQ ID No: 2 or any combination thereof; or 2) having at least 80% sequence identity with 1), and at least one of positions 6, 8, 10, 104 and 205 being different from positions 6, 8, 10, 104, and 205 in the amino acid sequence represented by SEQ ID No: 2. Provided are a nucleic acid molecule for encoding the polypeptide, a vector comprising the nucleic acid molecule, and a cell comprising the nucleic acid molecule or the vector. Provided are uses of the polypeptide, the nucleic acid molecule, the vector, and the cell.

13 Claims, 3 Drawing Sheets

Specification includes a Sequence Listing.

(56) References Cited

OTHER PUBLICATIONS

Seo et al., High-Level Expression of Recombinant Phospholipase C from Bacillus Cereus in Pichia Pastoris and its Characterization, Biotechnology Letters, 2004, 26(19):1475-1479.
Shang, Study of Bacillus Cereus Phospholipase C, Shandong Chemical Industry, 2016, 45(22):48, 49, 53.
PCT International Search Report and Written Opinion, PCT/CN2019/128973, Apr. 8, 2020, 22 pages.

* cited by examiner

SEQUENCE LISTING

<160> NUMBER OF SEQ ID NOS: 6

<210> SEQ ID NO 1
<211> LENGTH: 738
<212> TYPE: DNA
<213> ORGANISM: Artificial Sequence
<220> FEATURE:
<223> OTHER INFORMATION: nucleid acid sequence encoding PLC-N63DN131SN134D-Y56H

<400> SEQUENCE: 1

```
tggtcagctg aggacaagca taaggaaggt gtgaatagtc acttatggat cgtgaaccgt    60
gccattgata taatgtctag gaatacaact ctggttaagc aagatagagt tgctcaattg   120
aatgaatggc gtacagagct agagaatggc atctacgctg ctgatcatga aaacccctat   180
tacgatgaca gtaccttcgc ttctcacttt tacgatccag acaacggaaa gacatatatc   240
ccattcgcca agcaagctaa ggagactgga gctaagtact tcaagttggc tggagagtca   300
tacaagaata aagacatgaa gcaggccttc ttttatcttg ggttgtcatt gcattatttg   360
ggcgatgtca accaacctat gcatgccgca tcctttacgg acctgtccta tccacagggt   420
tttcactcca gtacgagaa ctttgtcgat actattaaag acaactacaa agttaccgat    480
gggaacggat attggaattg gaaaggcacc aaccctgaag aatggattca cggtgcagca   540
gtagttgcaa acaggacta ctctggaatt gtcaatgaca ataccaaaga ttggtttgtg    600
aaagccgcag tctcccagga atatgcagat aaatggagag ctgaagttac acctatgact   660
ggtaaacgac taatggatgc ccaaagagtt actgctggtt acattcaatt atggttcgac   720
acttacggtg acaggtaa                                                 738
```

<210> SEQ ID NO 2
<211> LENGTH: 245
<212> TYPE: PRT
<213> ORGANISM: Artificial Sequence
<220> FEATURE:
<223> OTHER INFORMATION: amino acid sequence of PLC-N63DN131SN134D-Y56H

<400> SEQUENCE: 2

```
Trp Ser Ala Glu Asp Lys His Lys Glu Gly Val Asn Ser His Leu Trp
1               5                   10                  15

Ile Val Asn Arg Ala Ile Asp Ile Met Ser Arg Asn Thr Thr Leu Val
            20                  25                  30

Lys Gln Asp Arg Val Ala Gln Leu Asn Glu Trp Arg Thr Glu Leu Glu
        35                  40                  45

Asn Gly Ile Tyr Ala Ala Asp His Glu Asn Pro Tyr Tyr Asp Asp Ser
    50                  55                  60

Thr Phe Ala Ser His Phe Tyr Asp Pro Asp Asn Gly Lys Thr Tyr Ile
65                  70                  75                  80

Pro Phe Ala Lys Gln Ala Lys Glu Thr Gly Ala Lys Tyr Phe Lys Leu
                85                  90                  95

Ala Gly Glu Ser Tyr Lys Asn Lys Asp Met Lys Gln Ala Phe Phe Tyr
            100                 105                 110

Leu Gly Leu Ser Leu His Tyr Leu Gly Asp Val Asn Gln Pro Met His
        115                 120                 125

Ala Ala Ser Phe Thr Asp Leu Ser Tyr Pro Gln Gly Phe His Ser Lys
    130                 135                 140

Tyr Glu Asn Phe Val Asp Thr Ile Lys Asp Asn Tyr Lys Val Thr Asp
145                 150                 155                 160
```

Gly Asn Gly Tyr Trp Asn Trp Lys Gly Thr Asn Pro Glu Glu Trp Ile
            165                 170                 175

His Gly Ala Ala Val Val Ala Lys Gln Asp Tyr Ser Gly Ile Val Asn
        180                 185                 190

Asp Asn Thr Lys Asp Trp Phe Val Lys Ala Ala Val Ser Gln Glu Tyr
            195                 200                 205

Ala Asp Lys Trp Arg Ala Glu Val Thr Pro Met Thr Gly Lys Arg Leu
        210                 215                 220

Met Asp Ala Gln Arg Val Thr Ala Gly Tyr Ile Gln Leu Trp Phe Asp
225                 230                 235                 240

Thr Tyr Gly Asp Arg
            245

<210> SEQ ID NO 3
<211> LENGTH: 738
<212> TYPE: DNA
<213> ORGANISM: Artificial Sequence
<220> FEATURE:
<223> OTHER INFORMATION: nucleic acid sequence encoding PLC-9-49

<400> SEQUENCE: 3
tggtcagctg aggaccctca tattgaaact gtgaatagtc acttatggat cgtgaaccgt      60
gccattgata taatgtctag gaatacaact ctggttaagc aagatagagt tgctcaattg     120
aatgaatggc gtacagagct agagaatggc atctacgctg ctgatcatga aaaccccctat    180 tacgatgaca gtaccttcgc ttctcacttt tacgatccag acaacggaaa gacatatatc    240
ccattcgcca agcaagctaa ggagactgga gctaagtact tcaagttggc tggagagtca    300
tacaagaatg gggacatgaa gcaggccttc ttttatcttg ggttgtcatt gcattatttg    360
ggcgatgtca accaacctat gcatgccgca tcctttacgg acctgtccta tccacagggt    420
tttcactcca gtacgagaa ctttgtcgat actattaaag acaactacaa agttaccgat    480
gggaacggat attggaattg gaaaggcacc aaccctgaag aatggattca cggtgcagca    540
gtagttgcaa acaggactat ctctggaatt gtcaatgaca ataccaaaga ttggtttgtg    600
aaagccgcag tctatcagga atatgcagat aaatggagag ctgaagttac acctatgact    660
ggtaaacgac taatggatgc ccaaagagtt actgctggtt acattcaatt atggttcgac    720
acttacggtg acaggtaa                                                 738

<210> SEQ ID NO 4
<211> LENGTH: 245
<212> TYPE: PRT
<213> ORGANISM: Artificial Sequence
<220> FEATURE:
<223> OTHER INFORMATION: amino acid sequence of PLC-9-49

<400> SEQUENCE: 4

Trp Ser Ala Glu Asp Pro His Ile Glu Thr Val Asn Ser His Leu Trp
1               5                   10                  15

Ile Val Asn Arg Ala Ile Asp Ile Met Ser Arg Asn Thr Thr Leu Val
            20                  25                  30

Lys Gln Asp Arg Val Ala Gln Leu Asn Glu Trp Arg Thr Glu Leu Glu
        35                  40                  45

Asn Gly Ile Tyr Ala Ala Asp His Glu Asn Pro Tyr Tyr Asp Asp Ser
    50                  55                  60

Thr Phe Ala Ser His Phe Tyr Asp Pro Asp Asn Gly Lys Thr Tyr Ile
65                  70                  75                  80

```
Pro Phe Ala Lys Gln Ala Lys Glu Thr Gly Ala Lys Tyr Phe Lys Leu
                85                  90                  95
Ala Gly Glu Ser Tyr Lys Asn Gly Asp Met Lys Gln Ala Phe Phe Tyr
            100                 105                 110
Leu Gly Leu Ser Leu His Tyr Leu Gly Asp Val Asn Gln Pro Met His
            115                 120                 125
Ala Ala Ser Phe Thr Asp Leu Ser Tyr Pro Gln Gly Phe His Ser Lys
            130                 135                 140
Tyr Glu Asn Phe Val Asp Thr Ile Lys Asp Asn Tyr Lys Val Thr Asp
145                 150                 155                 160
Gly Asn Gly Tyr Trp Asn Trp Lys Gly Thr Asn Pro Glu Glu Trp Ile
                165                 170                 175
His Gly Ala Ala Val Val Ala Lys Gln Asp Tyr Ser Gly Ile Val Asn
                180                 185                 190
Asp Asn Thr Lys Asp Trp Phe Val Lys Ala Ala Val Tyr Gln Glu Tyr
            195                 200                 205
Ala Asp Lys Trp Arg Ala Glu Val Thr Pro Met Thr Gly Lys Arg Leu
            210                 215                 220
Met Asp Ala Gln Arg Val Thr Ala Gly Tyr Ile Gln Leu Trp Phe Asp
225                 230                 235                 240
Thr Tyr Gly Asp Arg
                245

<210> SEQ ID NO 5
<211> LENGTH: 21
<212> TYPE: DNA
<213> ORGANISM: Artificial Sequence
<220> FEATURE:
<223> OTHER INFORMATION: Primer

<400> SEQUENCE: 5
gactggttcc aattgacaac g                                              21

<210> SEQ ID NO 6
<211> LENGTH: 24
<212> TYPE: DNA
<213> ORGANISM: Artificial Sequence
<220> FEATURE:
<223> OTHER INFORMATION: Primer

<400> SEQUENCE: 6
ggcaaatggc attctgacat cctc                                           24
```

POLYPEPTIDE HAVING PHOSPHOLIPASE C ACTIVITY AND USE THEREOF

CROSS-REFERENCE TO RELATED APPLICATIONS

This application represents the U.S. national stage entry of International Application No. PCT/CN2019/128973 filed Dec. 27, 2019, which claims priority to Chinese Patent Application No. 201811625457.6 filed Dec. 28, 2018, the disclosure of which is incorporated herein by reference in its entirety and for all purposes.

FIELD OF DISCLOSURE

The disclosure provides a polypeptide having phospholipase C activity and use thereof.

A Sequence Listing accompanies this application and is submitted as an ASCII text file of the sequence listing named "850766_00113_ST25.txt" which is 7,467 bytes in size and was created on Oct. 30, 2024. The sequence listing is electronically submitted via Patent Center and is incorporated herein by reference in its entirety.

BACKGROUND OF DISCLOSURE

Degumming is an important step in oil and fat refining. Traditional degumming by hydration is of high economic cost, high consumption of materials and energy and serious environmental pollution. In recent years, a lot of work has been devoted to apply enzymatic degumming in the degumming process of oil and fat refining. As compared to the traditional method, the method of degumming by enzyme has great advantages in environmental protection, economic effect, and quality, etc., as it could improve economic benefits, reduce energy consumption and emission and reduce the ecological environment pollution. One kind of enzymes used in degumming of oil and fat is phospholipase. Phospholipase C (PLC) exhibits significant advantages in, such as increasing yield of diacylglycerols (DAG) and reducing loss of oil yield, as compared to the other enzymes for degumming.

Phosphatidylcholine specific phospholipase C from *Bacillus cereus* (BC-PC-PLC) is a phospholipase C studied earlier. The full length of BC-PC-PLC is 283 amino acids, including a signal peptide of 24 amino acids and a leading peptide of 14 amino acids. The mature peptide is of 245 amino acids (see, e.g., Johansen, T., Holm, T., Guddal, P. H., Sletten, K., Haugli, F. B., Little, C. (1988). "Cloning and sequencing of the gene encoding the phosphatidylcholine-preferring phospholipase C of *Bacillus cereus*." Gene 65 (2): 293-304).

It was reported that the active sites of wild-type BC-PC-PLC were Glu4, Asp55, Tyr56, Glu146, Ser64, Thr65, Phe66, Phe70, Ile80, Thr133, Asn134, Leu135, Ser143 (see, e.g., Hough, e., Hansen, L. K., birknes, B., jynge, K., Hansen, S., hordvik, A., little, C., Dodson, e., derewenda, Z. (1989) "High-resolution (1.5 A) crystal structure of phospholipase C from *Bacillus cereus*." Nature. 338:357-60).

The crystal structure of BC-PC-PLC has been reported, which consists of multiple helix domains and at least three Zn2 binding sites, with the catalytic site at the aspartic acid at position 55 (see, e.g., Hough, e., Hansen, L. K., birknes, B., jynge, K., Hansen, S., hordvik, A., little, C., Dodson, e., derewenda, Z. (1989) "High-resolution (1.5 A) crystal structure of phospholipase C from *Bacillus cereus*." Nature. 338:357-60). Heterogenous expression of BC-PC-PLC was less studied. It has been reported that BC-PC-PLC was expressed in *Bacillus subtilis* and *Pichia pastoris* (see, for example, Durban, M. A., silbersack, J., schweder, T., Schauer, F., bornscheuer, U. T. (2007) High level expression of a recombinant phospholipase C from *Bacillus cereus* in *Bacillus subtilis*. Appl Microbiol Biotechnol 74 (3): 634-639; and Seo, K. H, Rhee J. I. (2004) High-level expression of recombinant phospholipase C from *Bacillus cereus* in *Pichia pastoris* and its characterization. Biotechnol Lett 26 (19): 1475-1479).

However, the thermal stability of the known phospholipase C is poor, which can not tolerate more than 60° C. Therefore, the optimal degumming temperature needs to be controlled at 50° C., which limits its disclosure in industry. If the thermal stability of phospholipase C can be effectively improved, it is in favor of the industrial disclosure of phospholipase C for reasons comprising: firstly, a higher temperature during degumming could reduce the viscosity of oil, improve the separation of oil and phospholipid, reduce the oil entrained in phospholipid, and further increase the yield of oil; secondly, at present, PLC and PLA1 are used in combination for deep degumming. CN201480017114.5 discloses a new PLA1 with the optimal degumming temperature of 65° C., so a more heat-resistant PLC is in favor of degumming together with the PLA1. In addition, sometimes the temperature of crude oil will exceed 50° C. during storage, especially in high temperature weather, so if the optimal reaction temperature of PLC is lower than 50° C., much cold water is needed to cool the crude oil, resulting in large energy consumption. Therefore, it is of great practical and economic value to develop a new polypeptide with thermostable phospholipase C activity.

SUMMARY OF DISCLOSURE

In the first aspect, the disclosure provides a polypeptide with phospholipase C activity, wherein the polypeptide has 1) an amino acid sequence set forth in SEQ ID No: 2 with amino acid substitutions at one or more positions, wherein the one or more positions are selected from the group consisting of: position 6, 8, 10, 104, 205 or any combination thereof of the amino acid sequence set forth in SEQ ID No: 2; or 2) at least 80%, preferably at least 85%, more preferably at least 90%, more preferably at least 95%, more preferably at least 97%, more preferably at least 98%, more preferably at least 99% identity with 1), and at least one of position 6, 8, 10, 104 and 205 is different from position 6, 8, 10, 104 and 205 of the amino acid sequence set forth in SEQ ID No: 2.

In some embodiments, amino acid substitutions occur at all of position 6, 8, 10, 104 and 205 of the amino acid sequence set forth in SEQ ID No: 2.

In some embodiments, the amino acid lysine at position 6 of the amino acid sequence set forth in SEQ ID No: 2 is substituted with proline, glycine, hydroxyproline, serine or threonine.

In some embodiments, the lysine at position 6 of the amino acid sequence set forth in SEQ ID No: 2 is substituted with proline.

In some embodiments, the amino acid lysine at position 8 of the amino acid sequence set forth in SEQ ID No: 2 is substituted with isoleucine, leucine, valine, methionine, alanine, phenylalanine or n-leucine.

In some embodiments, the lysine at position 8 of the amino acid sequence set forth in SEQ ID No: 2 is substituted with isoleucine.

In some embodiments, the amino acid glycine at position 10 of the amino acid sequence set forth in SEQ ID No: 2 is substituted with threonine or serine.

In some embodiments, the glycine at position 10 of the amino acid sequence set forth in SEQ ID No: 2 is substituted with threonine.

In some embodiments, the amino acid lysine at position 104 of the amino acid sequence set forth in SEQ ID No: 2 is substituted with glycine or proline.

In some embodiments, the lysine at position 104 of the amino acid sequence set forth in SEQ ID No: 2 is substituted with glycine.

In some embodiments, the amino acid serine at position 205 of the amino acid sequence set forth in SEQ ID No: 2 is substituted with tyrosine, tryptophan, phenylalanine, or threonine.

In some embodiments, the serine at position 205 of the amino acid sequence set forth in SEQ ID No: 2 is substituted with tyrosine.

In some embodiments, the amino acid sequence of the polypeptide comprises an amino acid sequence as set forth in SEQ ID No: 4.

In some embodiments, the amino acid sequence of the polypeptide consists of an amino acid sequence as set forth in SEQ ID No: 4.

In the second aspect, the disclosure provides an isolated polypeptide, wherein the polypeptide has 80%, preferably at least 85%, more preferably at least 90%, more preferably at least 95%, more preferably at least 97%, more preferably at least 98%, and more preferably at least 99% identity with the amino acid sequence set forth in the SEQ ID No: 4, and the isolated polypeptide has proline, isoleucine, threonine, glycine and tyrosine at amino acid residues corresponding to position 6, 8, 10, 104 and 205 of SEQ ID No: 4, respectively. Preferably, the polypeptide is obtained from *Bacillus subtilis*.

In the third aspect, the present disclosure provides a nucleic acid molecule encoding the polypeptide as described in the first or second aspect.

In some embodiments, the nucleic acid molecule comprises a nucleic acid sequence set forth in SEQ ID No: 3.

In some embodiments, the sequence of the nucleic acid molecule is as set forth in SEQ ID No: 3.

In the fourth aspect, the disclosure provides a vector containing the nucleic acid molecule as described in the third aspect.

In some embodiments, the vector is an expression vector.

In some embodiments, the vector is designed for expression in eukaryotic or prokaryotic cells.

In some embodiments, the vector is designed for expression in bacterial cells, fungal cells, yeast cells, mammalian cells, insect cells, or plant cells.

In the fifth aspect, the present disclosure provides a cell comprising a nucleic acid molecule as described in the third aspect or a vector as described in the fourth aspect.

In some embodiments, the cell is a eukaryotic cell or prokaryotic cell.

In some embodiments, the cell is a bacterial cell, fungal cell, yeast cell, mammalian cell, insect cell, or plant cell.

In the sixth aspect, the present disclosure provides phospholipase C produced by the cell as described in the fifth aspect.

In the seventh aspect, the disclosure provides use of a polypeptide as described in the first or second aspect, or a polypeptide encoded by a nucleic acid molecule as described in the third aspect, or a polypeptide encoded by a vector as described in the fourth aspect, or a fermentation broth, concentrate or polypeptide expressed by a cell as described in the fifth aspect, or phospholipase C as described in the sixth aspect as phospholipase C.

In some embodiments, the use is a use in oil and fat degumming.

In the eighth aspect, the disclosure provides an enzyme composition, which comprises a polypeptide as described in the first or second aspect, or a polypeptide encoded by a nucleic acid molecule as described in the third aspect, or a polypeptide encoded by a vector as described in the fourth aspect, or a polypeptide expressed by a cell as described in the fifth aspect, or phospholipase C as described in the sixth aspect, and at least one degumming enzyme.

In some embodiments, the at least one degumming enzyme is selected from the group consisting of: phospholipase $A_1$, phospholipase $A_2$, phospholipase B, phospholipase D, pectinase and mannanase.

In the ninth aspect, the disclosure provides use of a polypeptide as described in the first or second aspect, or a nucleic acid molecule as described in the third aspect, or a vector as described in the fourth aspect, or a cell as described in the fifth aspect, or an enzyme composition as described in the eighth aspect in the preparation of an enzyme for degumming.

DESCRIPTION OF SEQUENCE

Figure 1:
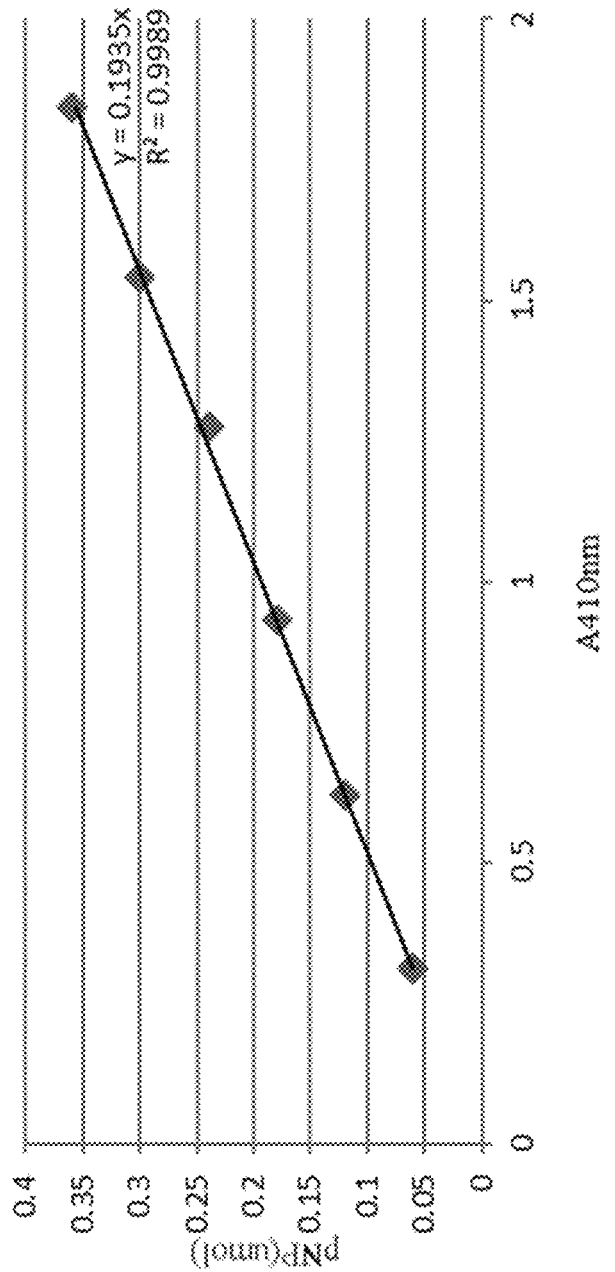
FIG. 1 is the standard curve of phospholipase activity.

SEQ ID No: 1 is the nucleic acid sequence encoding PLC-N63DN131SN134D-Y56H.

SEQ ID No: 2 is the amino acid sequence of PLC-N63DN131SN134D-Y56H.

SEQ ID No: 3 is the nucleic acid sequence encoding PLC-9-49.

SEQ ID No: 4 is the amino acid sequence of PLC-9-49.

DETAILED DESCRIPTION

Definition

As used herein, specific phosphatidylcholine phospholipase C and phosphatidylcholine-preferring phospholipase C have the same meaning and could readily be understood by those skilled in the art. As used herein, the abbreviation, PC-PLC, is meant to indicate specific phosphatidylcholine phospholipase C or phosphatidylcholine-preferring phospholipase C.

As used herein, an example of specific phosphatidylcholine phospholipase C is the specific phosphatidylcholine phospholipase C of *Bacillus cereus*, which is abbreviated as BC-PC-PLC herein. It should be understood that BC-PC-PLC can represent not only the wild-type specific phosphatidylcholine phospholipase C of *Bacillus cereus*, but also represent the mutant obtained based on such wild-type specific phosphatidylcholine phospholipase C herein.

In the case where the position of amino acid is indicated by numbers herein, the numbers refer to the amino acid position in SEQ ID No: 2. SEQ ID No: 2 is the amino acid sequence of specific phosphatidylcholine phospholipase C mutant PLC-N63DN131SN134D-Y56H of *Bacillus cereus*.

The internationally used single letter or three letter abbreviations of amino acids are used herein.

The terms "polypeptide", "peptide" and "protein" used herein can be used interchangeably to refer to a polymer formed by the connection of multiple amino acids through peptide bonds. The amino acids can be naturally-occurring amino acids or artificially synthesized analogs.

The terms "nucleic acid" and "polynucleotide" used herein can be used interchangeably, including but not limited to DNA, RNA, etc. The nucleotides can be naturally-occurring nucleotides or artificially synthesized analogs.

Cells as used herein may be eukaryotic cells or prokaryotic cells, for example, but not limited to bacterial cells, fungal cells, yeast cells, mammalian cells, insect cells or plant cells.

The term "conservative substitution" as used herein refers to a change in the amino acid composition of a protein that does not significantly alter the activity of the protein. Therefore, the "conservative substitution" of a specific amino acid sequence refers to the substitution of those amino acids that are not critical for protein activity, or the substitution of amino acids with other amino acids with similar properties (such as acidity, basicity, positive or negative charge, polarity or non polarity, etc.), so that even the substitution of critical amino acids will not significantly change the activity.

The term "random saturation mutagenesis" used herein refers to the process of using NNK degenerate codons in PCR primers for the site to be mutated, which can cover all 20 amino acids to achieve saturation mutagenesis. Meanwhile, because multiple sites are selected for the mutagenesis, the combination is random. This method is referred as random saturation mutagenesis in the disclosure.

It is well known in the art to provide conservative substitutions with amino acids having similar functions. For example, the alternative conservative amino acid substitutions for each amino acid are listed as follows:

The conservative substitution of alanine (ALA) is valine (Val)*, leucine (Leu) and isoleucine (Ile);

The conservative substitution of arginine (Arg) is lysine (Lys)*, glutamine (Gln) and asparagine (Asn);

The conservative substitution of asparagine (Asn) is glutamine (Gln)*, histidine (His), lysine (Lys), arginine (Arg) and aspartic acid (Asp);

The conservative substitution of aspartic acid (Asp) is glutamic acid (Glu)* and asparagine (Asn);

The conservative substitution of cysteine (Cys) is serine (Ser);

The conservative substitution of glutamine (Gln) is asparagine (Asn)*, histidine (His) and lysine (Lys);

The conservative substitution of glutamic acid (Glu) is aspartic acid (Asp)*, γ-Hydroxyglutamic acid (Gla);

The conservative substitution of glycine (Gly) is proline (Pro);

The conservative substitution of histidine (His) is asparagine (Asn), glutamine (Gln), lysine (Lys), arginine (Arg)*;

The conservative substitution of isoleucine (Ile) is leucine (Leu)*, valine (Val), methionine (Met), alanine (Ala), phenylalanine (Phe) and n-leucine (Nle);

The conservative substitution of leucine (Leu) is n-leucine (Nle), isoleucine (Ile)*, valine (Val), methionine (Met), alanine (Ala), phenylalanine (Phe);

The conservative substitution of lysine (Lys) is arginine (Arg)*, glutamine (Gln), asparagine (Asn) and ornithine (Orn);

The conservative substitution of methionine (Met) is leucine (Leu)*, isoleucine (Ile), phenylalanine (Phe) and n-leucine (Nle);

The conservative substitution of phenylalanine (Phe) is leucine (Leu)*, valine (Val), isoleucine (Ile) and alanine (Ala);

The conservative substitution of proline (Pro) is glycine (Gly)*, hydroxyproline (Hyp), serine (Ser), threonine (Thr);

The conservative substitution of serine (Ser) is threonine (Thr);

The conservative substitution of threonine (Thr) is serine (Ser); The conservative substitution of tryptophan (Trp) is tyrosine (Tyr);

The conservative substitution of tyrosine (Tyr) is tryptophan (Trp), phenylalanine (Phe)*, threonine (Thr) and serine (Ser);

The conservative substitution of valine (Val) is isoleucine (Ile), leucine (Leu)*, methionine (Met), phenylalanine (Phe), Alanine (Ala) and n-leucine (Nle).

Wherein * denotes the preferred conservative substitution.

In addition, see Creighton, Proteins: Structures and Molecular Properties, W.H. Freeman and company, New York (2nd ed., 1992).

Description of Embodiment

In the previous application CN201510946696.1 of the inventor, four amino acids of BC-PC-PLC (i.e. amino acids at positions 56, 63, 131 and 134) are mutated into histidine (Y56H), aspartic acid (N63D), serine (N131S) and aspartic acid (N134D), respectively. The mutated amino acid sequence is set forth in SEQ ID No: 2, and the coding sequence is set forth in SEQ ID No: 1, which is also called "PLC-N63DN131SN134D-Y56H" herein. The specific enzyme activity of PLC-N63DN131SN134D-Y56H is higher than that of wild-type BC-PC-PLC, but such mutant is not stable and cannot tolerate more than 60° C., with the optimum degumming temperature of 50° C., which limits the use of the mutant in industry.

Firstly, a higher temperature during degumming could reduce the viscosity of oil, improve the separation of oil and phospholipid, reduce the oil entrained in phospholipid, and further increase the yield of oil; secondly, at present, PLC and PLA1 are used in combination for deep degumming. CN201480017114.5 discloses a new PLA1 with the optimal degumming temperature of 65° C. (see paragraph of CN105073985A), so a more heat-resistant PLC is desired to cooperate with such degumming temperature in degumming together with the PLA1. In addition, sometimes the temperature of crude oil will exceed 50° C. during storage, especially in high temperature weather, so if the optimal reaction temperature of PLC is lower than 50° C., much cold water is needed to cool the crude oil, resulting in large energy consumption. Therefore, in order to improve the thermal stability and/or applicability of phospholipase C, the inventor has improved PLC-N63DN131SN134D-Y56H, and created various inventions of the present disclosure.

In the first aspect, the disclosure provides a polypeptide with phospholipase C activity. The polypeptide has 1) an amino acid sequence set forth in SEQ ID No: 2 with amino acid substitutions at one or more positions, wherein the one or more positions are selected from the group consisting of position 6, 8, 10, 104, 205 or any combination thereof of the amino acid sequence set forth in SEQ ID No: 2; or 2) at least 80%, preferably at least 85%, more preferably at least 90%, more preferably at least 95%, more preferably at least 97%, more preferably at least 98%, more preferably at least 99% identity with 1), and at least one of position 6, 8, 10, 104 and 205 is different from position 6, 8, 10, 104 and 205 of the amino acid sequence set forth in SEQ ID No: 2.

In some embodiments, amino acid substitutions occur at all positions 6, 8, 10, 104 and 205 in the amino acid sequence set forth in SEQ ID No: 2.

In some embodiments, the amino acid at position 6 of the amino acid sequence set forth in SEQ ID No: 2 is substituted with another amino acid.

In some embodiments, the amino acid at position 8 of the amino acid sequence set forth in SEQ ID No: 2 is substituted with another amino acid.

In some embodiments, the amino acid at position 10 of the amino acid sequence set forth in SEQ ID No: 2 is substituted with another amino acid.

In some embodiments, the amino acid at position 104 of the amino acid sequence set forth in SEQ ID No: 2 is substituted with another amino acid.

In some embodiments, the amino acid at position 205 of the amino acid sequence set forth in SEQ ID No: 2 is substituted with another amino acid.

In some embodiments, the amino acids at positions 6 and 8 of the amino acid sequence set forth in SEQ ID No: 2 are substituted with other amino acids.

In some embodiments, the amino acids at positions 6 and 10 of the amino acid sequence set forth in SEQ ID No: 2 are substituted with other amino acids.

In some embodiments, the amino acids at positions 6 and 104 of the amino acid sequence set forth in SEQ ID No: 2 are substituted with other amino acids.

In some embodiments, the amino acids at positions 6 and 205 of the amino acid sequence set forth in SEQ ID No: 2 are substituted with other amino acids.

In some embodiments, the amino acids at positions 8 and 10 of the amino acid sequence set forth in SEQ ID No: 2 are substituted with other amino acids.

In some embodiments, the amino acids at positions 8 and 104 of the amino acid sequence set forth in SEQ ID No: 2 are substituted with other amino acids.

In some embodiments, the amino acids at positions 8 and 205 of the amino acid sequence set forth in SEQ ID No: 2 are substituted with other amino acids.

In some embodiments, the amino acids at positions 10 and 104 of the amino acid sequence set forth in SEQ ID No: 2 are substituted with other amino acids.

In some embodiments, the amino acids at positions 10 and 205 of the amino acid sequence set forth in SEQ ID No: 2 are substituted with other amino acids.

In some embodiments, the amino acids at positions 104 and 205 of the amino acid sequence set forth in SEQ ID No: 2 are substituted with other amino acids.

In some embodiments, the amino acids at positions 6, 8 and 10 of the amino acid sequence set forth in SEQ ID No: 2 are substituted with other amino acids.

In some embodiments, the amino acids at positions 6, 8 and 104 of the amino acid sequence set forth in SEQ ID No: 2 are substituted with other amino acids.

In some embodiments, the amino acids at positions 6, 8 and 205 of the amino acid sequence set forth in SEQ ID No: 2 are substituted with other amino acids.

In some embodiments, the amino acids at positions 6, 10 and 104 of the amino acid sequence set forth in SEQ ID No: 2 are substituted with other amino acids.

In some embodiments, the amino acids at positions 6, 10 and 205 of the amino acid sequence set forth in SEQ ID No: 2 are substituted with other amino acids.

In some embodiments, the amino acids at positions 6, 104 and 205 of the amino acid sequence set forth in SEQ ID No: 2 are substituted with other amino acids.

In some embodiments, the amino acids at positions 8, 10 and 104 of the amino acid sequence set forth in SEQ ID No: 2 are substituted with other amino acids.

In some embodiments, the amino acids at positions 8, 10 and 205 of the amino acid sequence set forth in SEQ ID No: 2 are substituted with other amino acids.

In some embodiments, the amino acids at positions 8, 104 and 205 of the amino acid sequence set forth in SEQ ID No: 2 are substituted with other amino acids.

In some embodiments, the amino acids at positions 10, 104 and 205 of the amino acid sequence set forth in SEQ ID No: 2 are substituted with other amino acids.

In some embodiments, the amino acids at positions 6, 8, 10 and 104 of the amino acid sequence set forth in SEQ ID No: 2 are substituted with other amino acids.

In some embodiments, the amino acids at positions 6, 8, 10 and 205 of the amino acid sequence set forth in SEQ ID No: 2 are substituted with other amino acids.

In some embodiments, the amino acids at positions 6, 8, 104 and 205 of the amino acid sequence set forth in SEQ ID No: 2 are substituted with other amino acids.

In some embodiments, the amino acids at positions 6, 10, 104 and 205 of the amino acid sequence set forth in SEQ ID No: 2 are substituted with other amino acids.

In some embodiments, the amino acids at positions 8, 10, 104 and 205 of the amino acid sequence set forth in SEQ ID No: 2 are substituted with other amino acids.

In some embodiments, the amino acid lysine at position 6 of the amino acid sequence set forth in SEQ ID No: 2 is substituted with proline, glycine, hydroxyproline, serine or threonine.

In some embodiments, the lysine at position 6 of the amino acid sequence set forth in SEQ ID No: 2 is substituted with proline.

In some embodiments, the amino acid lysine at position 8 of the amino acid sequence set forth in SEQ ID No: 2 is substituted with isoleucine, leucine, valine, methionine, alanine, phenylalanine or n-leucine.

In some embodiments, the lysine at position 8 of the amino acid sequence set forth in SEQ ID No: 2 is substituted with isoleucine.

In some embodiments, the amino acid glycine at position 10 of the amino acid sequence set forth in SEQ ID No: 2 is substituted with threonine or serine.

In some embodiments, the amino acid glycine at position 10 of the amino acid sequence set forth in SEQ ID No: 2 is substituted with threonine.

In some embodiments, the amino acid lysine at position 104 of the amino acid sequence set forth in SEQ ID No: 2 is substituted with glycine or proline.

In some embodiments, the amino acid lysine at position 104 of the amino acid sequence set forth in SEQ ID No: 2 is substituted with glycine.

In some embodiments, the amino acid serine at position 205 of the amino acid sequence set forth in SEQ ID No: 2 is substituted with tyrosine, tryptophan, phenylalanine, or threonine.

In some embodiments, the serine at position 205 of the amino acid sequence set forth in SEQ ID No: 2 is substituted with tyrosine.

In some embodiments, the amino acid sequence of the polypeptide comprises an amino acid sequence as set forth in SEQ ID No: 4.

In some embodiments, the amino acid sequence of the polypeptide consists of an amino acid sequence as set forth in SEQ ID No: 4.

The present disclosure also considers functional variants of the polypeptide as described in the first aspect. In some embodiments, the functional variant is a conservative substitution variant.

In the second aspect, the disclosure provides an isolated polypeptide, wherein the polypeptide has at least 80%, preferably at least 85%, more preferably at least 90%, more preferably at least 95%, more preferably at least 97%, more preferably at least 98%, more preferably at least 99% identity with the amino acid sequence set forth in the SEQ ID No: 4, and the isolated polypeptide has proline, isoleucine, threonine, glycine and tyrosine at amino acid residues corresponding to positions 6, 8, 10, 104 and 205 of SEQ ID No: 4, respectively.

In some embodiments, the polypeptide is obtained from *Bacillus subtilis*.

In some embodiments, the polypeptide has at least 97%, at least 98%, at least 99%, at least 99.5% or higher identity with the amino acid sequence set forth in SEQ ID No: 4.

In some embodiments, the polypeptide has at least 97.2%, at least 97.6%, at least 98%, at least 98.4%, at least 98.8%, at least 99.2%, at least 99.6% or higher identity with the amino acid sequence set forth in SEQ ID No: 4.

In some embodiments, the amino acid residue of the isolated polypeptide corresponding to position 6 of SEQ ID No: 4 is proline.

In some embodiments, the amino acid residue of the isolated polypeptide corresponding to position 8 of SEQ ID No: 4 is isoleucine.

In some embodiments, the amino acid residue of the isolated polypeptide corresponding to position 10 of SEQ ID No: 4 is threonine.

In some embodiments, the amino acid residue of the isolated polypeptide corresponding to position 104 of SEQ ID No: 4 is glycine.

In some embodiments, the amino acid residue of the isolated polypeptide corresponding to position 205 of SEQ ID No: 4 is tyrosine.

In some embodiments, the amino acid residue of the isolated polypeptide corresponding to position 6 of SEQ ID No: 4 is proline, and/or the amino acid residue of the isolated polypeptide corresponding to position 8 of SEQ ID No: 4 is isoleucine, and/or the amino acid residue of the isolated polypeptide corresponding to position 10 of SEQ ID No: 4 is threonine, and/or the amino acid residue of the isolated polypeptide corresponding to position 104 of SEQ ID No: 4 is glycine, and/or the amino acid residue of the isolated polypeptide corresponding to position 205 of SEQ ID No: 4 is tyrosine.

In the third aspect, the present disclosure provides a nucleic acid molecule encoding the polypeptide as described in the first or second aspect. The disclosure considers different nucleic acid molecules that can be obtained based on the degeneracy of genetic codons or the codon preference of different species.

In some embodiments, the nucleic acid molecule comprises a nucleic acid sequence set forth in SEQ ID No: 3.

In some embodiments, the sequence of the nucleic acid molecule is set forth in SEQ ID No: 3.

In the fourth aspect, the disclosure provides a vector containing the nucleic acid molecule as described in the third aspect.

In some embodiments, the vector is an expression vector.

In some embodiments, the vector is designed for expression in a eukaryotic or prokaryotic cell.

In some embodiments, the vector is designed for expression in a bacterial cell, a fungal cell, a yeast cell, a mammalian cell, a insect cell, or a plant cell.

In some embodiments, the vector is a plasmid.

Suitable vectors for a eukaryotic cell or prokaryotic cell are well known to those skilled in the art, and a variety of original vectors are commercially available. Examples of vectors include but are not limited to a variety of vectors used in the examples of the present disclosure.

In the fifth aspect, the present disclosure provides a cell comprising a nucleic acid molecule as described in the third aspect or a vector as described in the fourth aspect.

In some embodiments, the cell is a eukaryotic cell or prokaryotic cell.

In some embodiments, the cell is a bacterial cell, fungal cell, yeast cell, mammalian cell, insect cell, or plant cell.

In some embodiments, the cell is a *Pichia pastoris* cell.

In some embodiments, the cell is a *Bacillus subtilis* cell.

In some embodiments, the cell is a *Escherichia coli* cell.

With regard to the cell containing the nucleic acid molecule of the present disclosure, the nucleic acid molecule can be located outside chromosomes (for example, in a vector) or integrated into a chromosome of a host cell. It is well known to those skilled in the art that how to integrate a nucleic acid molecule into chromosomes of a host cell and how to introduce a vector into a host cell through transformation or transfection.

In the sixth aspect, the present disclosure provides phospholipase C produced by the cell as described in the fifth aspect. It is well known to those skilled in the art to produce a target peptide or protein by a genetically engineered host cell.

In the seventh aspect, the present disclosure provides use of a polypeptide as described in the first or second aspect, or a polypeptide encoded by a nucleic acid molecule as described in the third aspect, or a polypeptide encoded by a vector as described in the fourth aspect, or a fermentation broth, a concentrate or a polypeptide expressed by a cell as described in the fifth aspect, or a phospholipase C as described in the sixth aspect as phospholipase C.

In some embodiments, the use is a use in oil and fat degumming process.

The application of specific phosphatidylcholine phospholipase C in oil and fat degumming process is known in the art. Phospholipase C can hydrolyze the glial component phospholipid in oil to produce hydrophilic phosphate part and lipophilic DAG. The glial part is removed as the hydrophilic part is taken away by water. DAG increases the yield of oil. For example, the enzymatic degumming process comprises heating the crude oil to 60° C., adding phospholipase C solution, stirring in the reactor for 2h after high-speed shear mixing, and then centrifuging to separate the water phase and oil phase.

In the eighth aspect, the disclosure provides an enzyme composition, which comprises a polypeptide as described in the first or second aspect, or a polypeptide encoded by a nucleic acid molecule as described in the third aspect, or a polypeptide encoded by a vector as described in the fourth aspect, or a polypeptide expressed by a cell as described in the fifth aspect, or phospholipase C as described in the sixth aspect, and at least one degumming enzyme.

In some embodiments, the at least one degumming enzyme is selected from the group consisting of: phospholipase $A_1$, phospholipase $A_2$, phospholipase B, phospholipase D, pectinase and mannanase.

In some embodiments, the enzyme composition comprises a polypeptide as described in the first or second aspect and at least one degumming enzyme.

In some embodiments, the enzyme composition comprises a polypeptide encoded by a nucleic acid molecule as described in the third aspect and at least one degumming enzyme.

In some embodiments, the enzyme composition comprises a polypeptide encoded by a vector as described in the fourth aspect and at least one degumming enzyme.

In some embodiments, the enzyme composition comprises a polypeptide expressed by a cell as described in the fifth aspect and at least one degumming enzyme.

In some embodiments, the enzyme composition comprises phospholipase C as described in the sixth aspect and at least one degumming enzyme.

In some embodiments, the enzyme composition comprises a polypeptide as described in the first or second aspect, and/or a polypeptide encoded by a nucleic acid molecule as described in the third aspect, and/or a polypeptide encoded by a vector as described in the fourth aspect, and/or a polypeptide expressed by a cell as described in the fifth aspect, and/or phospholipase C as described in the sixth aspect, and at least one degumming enzyme.

In the ninth aspect, the disclosure provides use of a polypeptide as described in the first or second aspect, or a nucleic acid molecule as described in the third aspect, or a vector as described in the fourth aspect, or a cell as described in the fifth aspect, or an enzyme composition as described in the eighth aspect in the preparation of an enzyme for degumming.

It should be understood that the above detailed description is only for clear understanding of the content of the present disclosure by those skilled in the art, and is not intended to limit it in any aspect. Those skilled in the art would make various changes to the embodiments.

Example

The following examples are provided to further describe the present disclosure without any limitation.
Experimental Materials
The main materials used in the examples of the present disclosure are as follows:
1. Strain
Pichia pastoris SMD1168 (Invitrogen, Cat. No. C17500), Escherichia coli DH5α(TAKARA, Cat. No. D9057A).

2. Culture Medium and Solution
LB liquid medium: 0.5% yeast extract, 1% tryptone, 1% NaCl, pH 7.0.
LB solid medium: LB liquid medium with 1.5% agar added.
YPD liquid medium: 1% yeast extract, 2% peptone, 2% glucose.
YPD solid medium: LB liquid medium with 2% agar added.
MGYS solid medium: 1.34% yeast nitrogen base (YNB) (containing ammonium sulfate and no amino acid), 1% glycerol, 1M sorbitol, $4×10^{-5}$% D-biotin, 2% agar.
BMM-soybean phospholipid screening medium: 1.34% yeast nitrogen base (YNB) (containing ammonium sulfate, without amino acid), $4×10^{-5}$% D-biotin, 0.5% methanol (added after sterilization), 2% soybean lecithin emulsion, 0.1M citric acid sodium citrate buffer (pH=6.6), 2% agar, and 10 μM $ZnSO_4·7 H_2O$ added.
Preparation of 2% soybean phospholipid emulsion: 2 g soybean phospholipid and 100 ml $H_2O$ were weighed and homogenized at 8000 rpm with a highspeed homogenizer for 1 min.
BMGY liquid medium: 1% yeast extract, 2% peptone, 1.34% yeast nitrogen base (YNB) (containing ammonium sulfate, without amino acid), 1% glycerol, $4×10^{-5}$% D-biotin, 0.1 M potassium dihydrogen phosphate-dipotassium hydrogen phosphate buffer (pH=6.0).
BMMY liquid medium: 1% yeast extract, 2% peptone, 1.34% yeast nitrogen base (YNB) (containing ammonium sulfate and no amino acid), 0.3% $ZnSO_4·7 H_2O$, 0.5% methanol (added after sterilization), $4×10^{-5}$% D-biotin (added after sterilization), 0.1 M citric acid-sodium citrate buffer (pH=6.6).
3. Enzyme Activity Determination: pNPPC Method
3.1 Plotting the Standard Curve of Phospholipase Activity
0.01391 g p-nitrophenol was weighed and dissolved in 50 ml sterile water to prepare 2 mmol/L working solution. See table 1, various reagents were added, a standard curve was made, and the obtained standard curve was set forth in FIG. 1. The condition for determining the enzyme activity of a sample was consistent with that for making the standard curve.

TABLE 1

The amounts of the reagents added when plotting the standard curve of phospholipase activity.

| No. | 1 | 2 | 3 | 4 | 5 | 6 | 7 |
|---|---|---|---|---|---|---|---|
| 2.0 mmol/L pNP (μl) | 0 | 7.5 | 15 | 22.5 | 30 | 37.5 | 45 |
| dd$H_2O$ (μl) | 62.5 | 55 | 47.5 | 40 | 32.5 | 25 | 17.5 |
| Substrate buffer (ml) | 562.5 | 562.5 | 562.5 | 562.5 | 562.5 | 562.5 | 562.5 |
| pNP total (umol) | 0 | 0.06 | 0.12 | 0.18 | 0.24 | 0.30 | 0.36 |

After the above solutions were mixed, it was treated at 37° C. for 15 minutes, then 500 μl of 0.5N NaOH was added. The absorbance at 410 nm was measured.
3.2 Preparation of Reaction Buffer
0.1 M boric acid-sodium borate buffer (pH=7.6) containing 20 mm pNPPC.
600 μL of above buffer was taken, 25 μl was added, and reacted at 37° C. for 15 min, then 500 μl of 0.5N NaOH was added. The reaction was stoped and the absorbance at 410 nm was determined.
4. Calculation of Enzyme Activity
The enzyme activity was calculated according to the following formula:
Sample enzyme activity (U/ml)=A (absorbance at 410 nm)×0.1935×dilution factor×10/15

5. Protein Concentration Assay Reagents:
Modified Bradford protein concentration assay kit (available from Shanghai Sangon Bioengineering Co., Ltd.).
6. Enzymes Used in Experiment:
Sal I (available from New England Biotechnology (Beijing) Co., Ltd.);
DNA polymerase: PrimeSTAR®HS DNA polymerase (available from Takara (Dalian) Co., Ltd.);
T4 DNA ligase (available from Fermentas Co., Ltd.).

Example 1: Construction and Screening of Phospholipase C Mutant Library pmAO-PLC-N63DN131SN134D-Y56H vector was prepared according to the method described in CN 201510946696.1.

pmAO-PLC-N63DN131SN134D-Y56H vector was used as template, the library of amino acids at positions 6, 8, 10, 104 and 205 for random saturation mutagenesis was constructed by Synbio Technologies (Suzhou) Co., Ltd. The plasmid library was transformed into *E. coli* DH5a, and all the obtained *E. coli* clones were washed into LB liquid medium (containing 100 μg/ml ampicillin), cultured at 37° C. for 4 h. The plasmid was extracted and linearized with SalI, and about 8.5 KB fragment was recovered. 500 ng vector was taken and transformed into the competent cells of *Pichia pastoris* M314 strain by electroporation. The transformants were inoculated on MGYS plates and incubated at 30° C. for three days to obtain the *Pichia pastoris* mutant library of PLC-N63DN131SN134D-Y56H. Monoclones on the plate were picked out and inoculated on the BMM-soybean phospholipid screening plate. The clones with large white precipitate circle were selected. The mutant strain was obtained and designated as PLC-9-49.

Example 2: Sequence Analysis of Phospholipase C Mutant

The PLC-9-49 strain was inoculated in 3 ml YPD liquid medium at 30° C. overnight, and then the genomic DNA was extracted. The genomic DNA of PLC-9-49 strain was used as template. PCR amplification was conducted with PrimeSTAR®HS DNA polymerase and a primer pair of AOX1-5/AOX1-3 to obtain the DNA sequence of PLC-9-49 strain, wherein, The sequence of primer AOX1-5 was 5'-GACTGGTTC-CAATTGACAACG-3' (SEQ ID NO: 5);

The sequence of primer AOX1-3 was 5'-GGCAAATGG-CATTCTGACATCCTC-3' (SEQ ID NO: 6).

The obtained sequences were sent to Shanghai Sangon Bioengineering Co., Ltd. and sequenced with the primer pair of AOX1-5/AOX1-3. The result of DNA sequencing of PLC-9-49 is set forth in SEQ ID No: 3. After alignment, compared with the SEQ ID No: 1, several bases in the SEQ ID No: 3 were mutated, wherein the lysine at position 6 was mutated to proline, the lysine at position 8 was mutated to isoleucine, the glycine at position 10 was mutated to threonine, the lysine at position 104 was mutated to glycine, and the serine at position 205 was mutated to tyrosine. The amino acid sequence of PLC-9-49 is set forth in SEQ ID No: 4.

Example 3: Thermal Stability Analysis of PLC-9-49 Mutant

Strain PLC-9-49 and strain PLC-N63DN131SN134D-Y56H were taken and activated in liquid YPD, and then inoculated in BMGY medium at 30° C. overnight at 220 rpm. The culture was transferred to BMMY medium, wherein the initial $OD_{600}$ was 6.

First, induction is was performed with 2% methanol, supplemented with 1% methanol after 48 h and 56 h, respectively, and sampled at 72 h. The obtained samples were concentrated by 40-fold by ultrafiltration desalting with ultrafiltration tubes having a molecular weight cut-off of 40 kDa. The treated samples were added to a buffer (20 mM citric acid-sodium citrate buffer (pH 6.6), 10 uM ZnSO4).

The fermentation broth concentrated by ultrafiltration was kept at 60° C., 65° C., 70° C. and 75° C. for 2h, and 0.5 μl of fermentation broth concentrate was added to 600 μl pNPPC reaction buffer and reacted at 37° C. for 15 min, then 500 μl of 0.5N NaOH was added to stop the reaction, and the absorbance was measured at 410 nm. According to the standard curve, the activity of phospholipase C was calculated for each fermentation sample.

Figure 2:
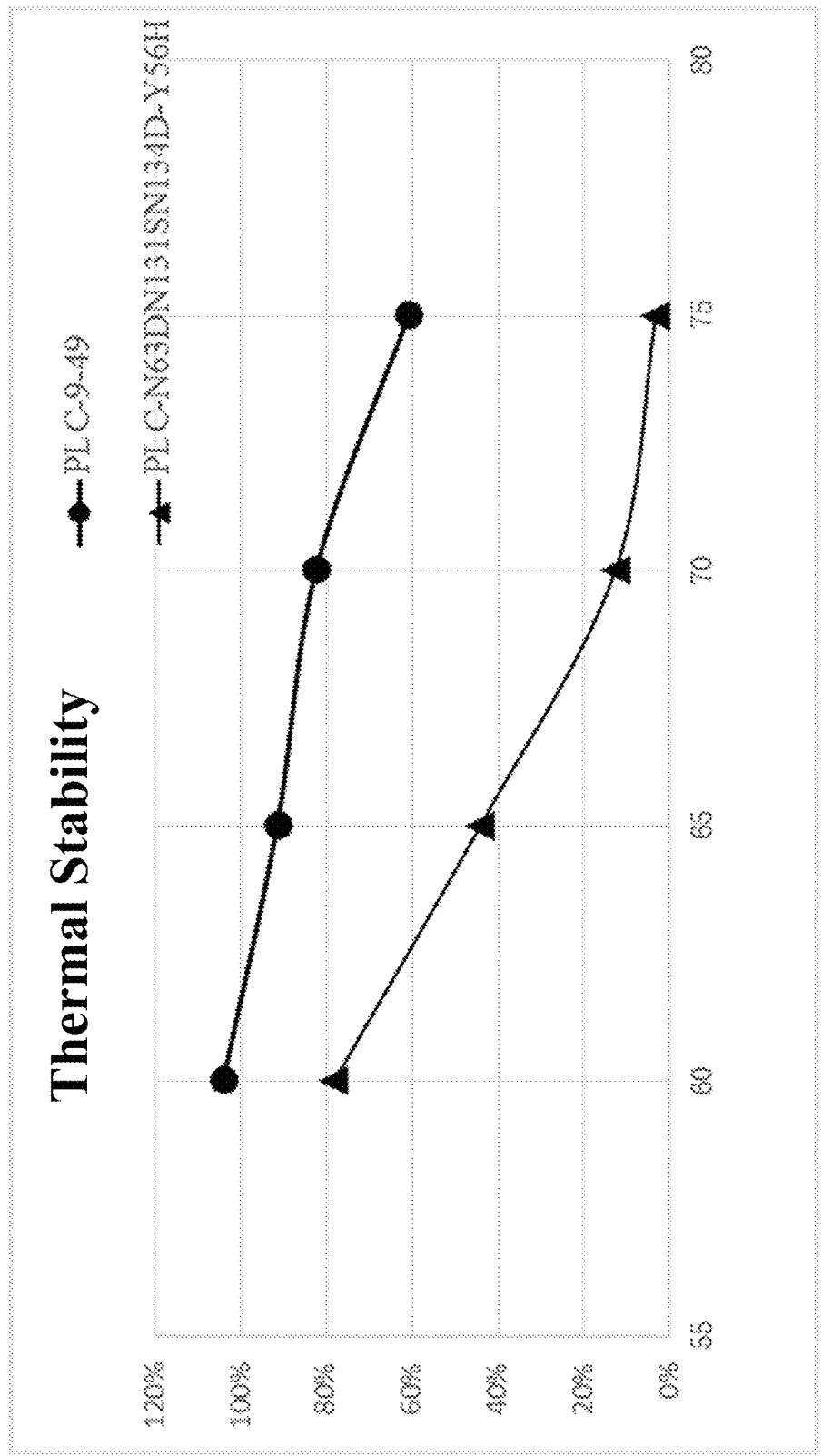
FIG. 2 shows the thermal stability comparison between PLC-9-49 and PLC-N63DN131SN134D-Y56H, wherein the circles represent PLC-9-49 and the triangles represent PLC-N63DN131SN134D-Y56H.

The thermal stability of PLC-9-49 and PLC-N63DN131SN134D-Y56H was shown in FIG. 2. After treating at 60° C. for 2 h, the vitality of PLC-9-49 mutant remained 91%, while the vitality of PLC-N63DN131SN134D-Y56H was decreased to 44%. After treating at 70° C. for 2 h, the vitality of PLC-9-49 mutant remained 83%, while the vitality of PLC-N63DN131SN134D-Y56H was decreased to 13%. After treating at 75° C. for 2 h, the vitality of PLC-9-49 mutant remained 61%, while the vitality of PLC-N63DN131SN134D-Y56H was decreased to 3%.

It can be seen that the thermal stability of PLC-9-49 is significantly higher than that of PLC-N63DN131SN134D-Y56H.

Figure 3:
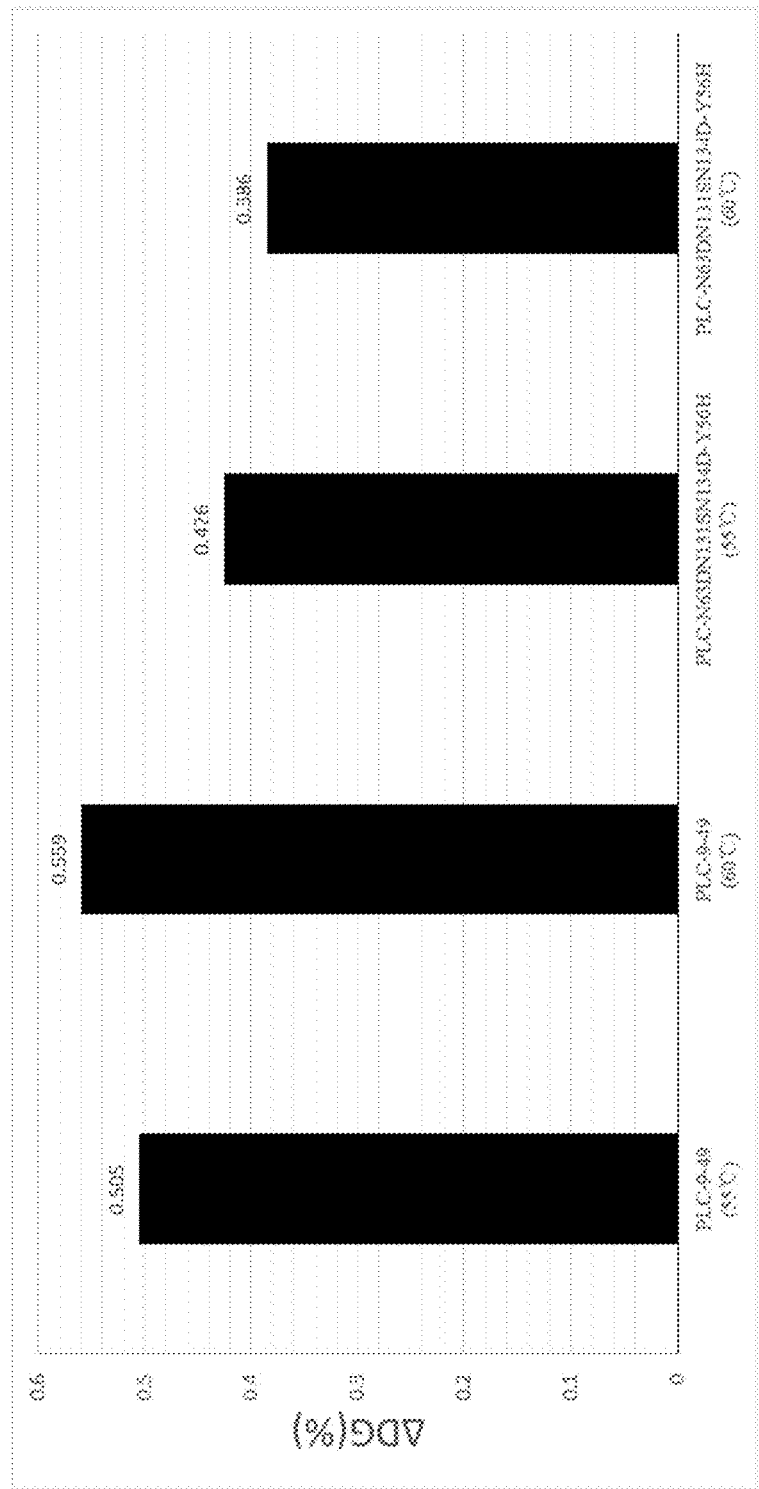
FIG. 3 shows the DAG increment of degumming by PLC-9-49 and PLC-N63DN131SN134D-Y56H at 55° C. and 60° C., respectively, as compared with crude oil.

Example 4: PLC-9-49 Degumming Test 100 g crude soybean oil was heated to 55° C. and 60° C., respectively for degumming. 50 ppm PLC-9-49 and PLC-N63DN131SN134D-Y56H samples were added respectively to obtain an aqueous phase of 3% in the system, and sheared for 1 min by high-speed shear machine (10000 r/min), stirred at 55° C. and 60° C. (750 r/min) for 2 h, heated to 85° C. and kept for 5 min. The sample was centrifuged at 12000 rpm for 10 min, and about 10 g of upper oil sample was taken. DAG level was determined by HPLC. The DAG increment of PLC-9-49 sample and PLC-N63DN131SN134D-Y56H sample relative to crude oil was shown in FIG. 3. Degumming using PLC-9-49 at 60° C. increases the increment of DAG by about 10% as compared with 55° C., while degumming using PLC-N63DN131SN134D-Y56H at 60° C. decreases the increment of DAG by 9.4% as compared with 55° C.

It can be seen that the degumming temperature of PLC-9-49 is about 5° C. higher than that of PLC-N63DN131SN134D-Y56H. Therefore, the industrial applicability of PLC-9-49 is better.

We claim:

1. A mutant phospholipase C polypeptide, wherein the polypeptide sequence has at least 95% identity with the amino acid sequence of SEQ ID NO:4, and has proline, isoleucine, threonine, glycine, and tyrosine, respectively, at positions 6, 8, 10, 104, and 205, with reference to SEQ ID NO: 4.

2. A nucleic acid molecule encoding the polypeptide according to claim 1.

3. A vector comprising the nucleic acid molecule according to claim 2.

4. A cell comprising the nucleic acid molecule according to claim 2 or an expression vector comprising the nucleic acid molecule.

5. An enzyme composition, comprising the polypeptide according to claim 1 and at least one degumming enzyme.

6. The mutant phospholipase C polypeptide according to claim 1, wherein the amino acid sequence of the polypeptide consists of the amino acid sequence of SEQ ID NO: 4.

7. The mutant phospholipase C polypeptide according to claim 1, expressed from a *Bacillus subtilis* host cell.

8. The nucleic acid molecule according to claim 2, comprising or consisting of the nucleic acid sequence of SEQ ID NO: 3.

9. The cell according to claim 4, wherein the cell is a bacterial cell, a fungal cell, a yeast cell, a mammalian cell, an insect cell or a plant cell.

10. The enzyme composition of claim 5, wherein the at least one degumming enzyme is selected from the group consisting of: phospholipase $A_1$, phospholipase $A_2$, phospholipase B, phospholipase D, pectinase and mannanase.

11. The enzyme composition of claim 5, wherein the amino acid sequence of the polypeptide consists of the amino acid sequence of SEQ ID No: 4.

12. An enzyme composition comprising a polypeptide encoded by a nucleic acid molecule encoding the polypeptide according to claim 1, or encoded by a vector comprising the nucleic acid molecule, or expressed by a cell comprising the nucleic acid molecule or the vector, and at least one degumming enzyme, wherein the at least one degumming enzyme is selected from the group consisting of: phospholipase $A_1$, phospholipase $A_2$, phospholipase B, phospholipase D, pectinase and mannanase.

13. An enzyme composition comprising the phospholipase C according to claim 1 and at least one degumming enzyme, wherein the at least one degumming enzyme is selected from the group consisting of: phospholipase A1, phospholipase A2, phospholipase B, phospholipase D, pectinase and mannanase.

\* \* \* \* \*